(12) United States Patent
Kamme et al.

(10) Patent No.: US 7,056,673 B2
(45) Date of Patent: Jun. 6, 2006

(54) PRESERVATION OF RNA IN A BIOLOGICAL SAMPLE

(75) Inventors: Fredrik C. Kamme, San Diego, CA (US); Bernhard H Meurers, San Diego, CA (US); Dmitri Talantov, San Diego, CA (US); Jingxue Yu, San Diego, CA (US)

(73) Assignee: Janssen Pharmaceutica N.V., Beerse (BE)

( * ) Notice: Subject to any disclaimer, the term of this patent is extended or adjusted under 35 U.S.C. 154(b) by 0 days.

(21) Appl. No.: 10/826,834

(22) Filed: Apr. 15, 2004

(65) Prior Publication Data

US 2004/0259133 A1    Dec. 23, 2004

Related U.S. Application Data

(60) Provisional application No. 60/465,307, filed on Apr. 25, 2003.

(51) Int. Cl.
*C12Q 1/68* (2006.01)
*C07H 21/02* (2006.01)
*C07H 21/04* (2006.01)

(52) U.S. Cl. .................... 435/6; 536/23.1; 536/24.3
(58) Field of Classification Search .................. 435/6; 536/23.1, 24.3
See application file for complete search history.

(56) References Cited

U.S. PATENT DOCUMENTS

| | | | |
|---|---|---|---|
| 4,943,531 A | 7/1990 | Goff et al. | |
| 5,242,974 A | 9/1993 | Holmes | |
| 5,322,770 A | 6/1994 | Gelfand | |
| 5,384,261 A | 1/1995 | Winkler et al. | |
| 5,405,776 A | 4/1995 | Kotewicz et al. | |
| 5,405,783 A | 4/1995 | Pirrung et al. | |
| 5,412,087 A | 5/1995 | McGall et al. | |
| 5,424,186 A | 6/1995 | Fodor et al. | |
| 5,429,807 A | 7/1995 | Matson et al. | |
| 5,436,327 A | 7/1995 | Southern et al. | |
| 5,445,934 A | 8/1995 | Fodor et al. | |
| 5,472,672 A | 12/1995 | Brennan | |
| 5,527,681 A | 6/1996 | Holmes | |
| 5,529,756 A | 6/1996 | Brennan | |
| 5,532,128 A | 7/1996 | Eggers et al. | |
| 5,545,531 A | 8/1996 | Rava et al. | |
| 5,554,501 A | 9/1996 | Coassin et al. | |
| 5,556,752 A | 9/1996 | Lockhart et al. | |
| 5,561,071 A | 10/1996 | Hollenberg et al. | |
| 5,571,639 A | 11/1996 | Hubbell et al. | |
| 5,593,839 A | 1/1997 | Hubbell et al. | |
| 5,599,695 A | 2/1997 | Pease et al. | |
| 5,624,711 A | 4/1997 | Sundberg et al. | |
| 5,658,734 A | 8/1997 | Brock et al. | |
| 5,700,637 A | 12/1997 | Southern | |
| 5,807,522 A * | 9/1998 | Brown et al. ................. | 422/50 |
| 6,004,755 A | 12/1999 | Wang | |
| 6,204,375 B1 * | 3/2001 | Lader .......................... | 536/25.4 |
| 6,420,132 B1 | 7/2002 | Bonner et al. | |
| 2002/0009768 A1 | 1/2002 | Chu | |
| 2002/0102666 A1 * | 8/2002 | Reiter et al. ................. | 435/110 |
| 2002/0177149 A1 * | 11/2002 | Rimm et al. ................. | 435/6 |
| 2002/0197637 A1 * | 12/2002 | Wilson et al. ................ | 435/6 |
| 2003/0152928 A1 * | 8/2003 | Asai et al. .................... | 435/6 |

FOREIGN PATENT DOCUMENTS

WO    WO9521944    8/1995

OTHER PUBLICATIONS

Adams, "Binding Of Crystal Violet By Nucleic Acids of *Escherichia coli*", *J. Pharm. Pharmacol.*, vol. 20, Suppl: pp. 18S-22S (1968).

Amann et al., "Identification In Situ And Phylogeny Of Uncultured Bacterial Endosymbionts", *Nature*, vol. 351, pp. 161-164 (1991).

Armstrong et al., "A Comparison Of The Interaction Of An Acridine Dye And A Triphenylmethane Dye With Deoxyribonucleic Acid", *J. Am. Chem. Soc.*, vol. 94(22), pp. 7650-7653 (1972).

Boonacker et al., "Enzyme Cytochemical Techniques For Metabolic Mapping In Living Cells, With Special Reference To Proteolysis", *J. Histochem. Cytochem.*, vol. 49(12), pp. 1473-1486 (2001).

Danguy, "Perspectives In Modern Glycohistochemistry", *Eur. J. Histochem.*, vol. 39, pp. 5-14 (1995).

Eltoum et al., "Microdissection Of Histologic Sections: Past, Present, And Future",*Adv. Anat. Pathol.*, vol. 9(5), pp. 316-322 (2002).

Emmert-Buck et al., "Laser Capture Microdissection", *Science*, vol. 274, pp. 998-1001 (1996).

(Continued)

*Primary Examiner*—Ethan Whisenant (57) ABSTRACT

To preserve RNA in a biological sample for analysis, the sample is incubated with an RNA preservative capable of precipitating RNA in an aqueous solution, such as a triphenylmethane dye (e.g., methyl green, crystal violet, pararosaniline, or tris-(4-aminophenyl)methane), cresyl violet, or cobalt ions. RNA preservation may be used in an immunostaining assay and other histochemical methods.

4 Claims, 5 Drawing Sheets

OTHER PUBLICATIONS

Fend et al., "Immuno-LCM: Laser Capture Microdissection Of Immunostained Frozen Sections For mRNA Analysis", *Am. J. Pathol.*, vol. 154(1), pp. 61-66 (1999).

Fink et al., "Immunostaining And Laser-Assisted Cell Picking For mRNA Analysis," *Lab. Invest.*, vol. 80(3), pp. 327-333 (2000).

Fox et al., "Methyl Green And Its Analogues Bind Selectively To AT-Rich Regions Of Native DNA", *Eur. J. Histochem.*, vol. 36, pp. 263-270 (1992).

Goldsworthy et al., "Effects Of Fixation On RNA Extraction And Amplification From Laser Capture Microdissected Tissue", *Mol. Carcinog.*, vol. 25, pp. 86-91 (1999).

Graeber et al., "Axotomy Of The Rat Facial Nerve Leads To Increased CR3 Complement Receptor Expression By Activated Microglial Cells", *J. Neurosci. Res.*, vol. 21, pp. 18-24 (1988).

Jiang et al., "Use Of Interphase Fluorescence In Situ Hybridization As A Powerful Diagnostic Tool In Cytology", *Diagn. Mol. Pathol.*, vol. 11(1), pp. 47-57 (2002).

Kim et al., "Methyl Green. A DNA Major-Groove Binding Drug", *FEBS Lett.*, vol. 315(1), pp. 61-64 (1993).

Kohda et al., "Analysis Of Segmental Renal Gene Expression By Laser Capture Microdissection", *Kidney Int.*, vol. 57, pp. 321-331 (2000).

Krizman et al., "Construction Of A Representative cDNA Library From Prostatic Intraepithelial Neoplasia", *Cancer Res.*, vol. 56, pp. 5380-5383 (1996).

Leethanakul et al., "Distinct Pattern Of Expression Of Differentiation And Growth-Related Genes In Squamous Cell Carcinomas Of The Head And Neck Revealed By The Use Of Laser Capture Microdissection And cDNA Arrays", *Oncogene*, vol. 19, pp. 3220-3224 (2000).

McNicol et al., "In Situ Hybridization And Its Diagnostic Applications In Pathology", *J. Pathol.*, vol. 182, pp. 250-261 (1997).

Melnick et al., "The Mechanism Of The Drug Induced Partial Displacement Of Methyl Green From DNA", *Biochem Int.*, vol. 16, pp. 69-75 (1988).

Muller et al., "Interactions Of Heteroaromatic Compounds With Nucleic Acids. A-T-Specific Non-Intercalating DNA Ligands", *Eur. J. Biochem.*, vol. 54, pp. 385-394 (1975).

Murakami et al., "IF-LCM: Laser Capture Microdissection Of Immunofluorescently Defined Cells For mRNA Analysis", *Kidney Int.*, vol. 58, pp. 1346-1353 (2000).

Okuducu et al., "Influence Of Histochemical Stains On Quantitative Gene Expression Analysis After Laser-Assisted Microdissection", *Int. J. Mol. Med.*, vol 11, pp. 449-453 (2003).

Pabon et al., "Optimized T7 Amplification System For Microarray Analysis", *Biotechniques*, vol. 31(4), pp. 874-879 (2001).

Quan et al., "Induction Of Inhibitory Factor KappaBalpha mRNA In The Central Nervous System After Peripheral Lipopolysaccharide Administration: An In Situ Hybridization Histochemistry Study In The Rat", *Proc. Natl. Acad. Sci. USA*, vol. 94, pp. 10985-10990 (1997).

Sagar et al., "Expression Of c-Fos Protein In Brain: Metabolic Mapping At The Cellular Level", *Science*, vol. 240, pp. 1328-1331 (1988).

Schutze et al., "Identification Of Expressed Genes By Laser-Mediated Manipulation Of Single Cells", *Nat. Biotechnol.*, vol. 16, pp. 737-742 (1998).

Smith et al., "Fluorescence Detection In Automated DNA Sequence Analysis", *Nature*, vol. 321, pp. 674-679 (1986).

Sovago et al., "An Overview On Functional Receptor Autoradiography Using [35S]GTPgammaS", *Brain Res. Rev.*, vol. 38, pp. 149-164 (2001).

Streit, An Improved Staining Method For Rat Microglial Cells Using The Lectin From *Griffonia simplicifolia* (GSA I-B4), *J. Histochem. Cytochem.*, vol. 38(11), pp. 1683-1686 (1990).

Swanson, "Foundations Of Immunohistochemistry. A Practical Review", *Am. J. Clin. Pathol.*, vol. 90(3), pp. 333-339 (1988).

Vijayanathan et al., "DNA Condensation By Polyamines: A Laser Light Scattering Study Of Structural Effects", *Biochemistry*, vol. 40, pp. 13644-13651 (2001).

Vocke et al., "Analysis Of 99 Microdissected Prostate Carcinomas Reveals A High Frequency Of Allelic Loss On Chromosome 8p12-21", *Cancer Res.*, vol. 56(10), pp. 2411-2416 (1996).

Yang et al., "Design Issues For cDNA Microarray Experiments", *Nature Reviews*, vol. 3, pp. 579-588 (2002).

* cited by examiner

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial
<220> FEATURE:
<223> OTHER INFORMATION: PCR primer

<400> SEQUENCE: 1
cctccactgg catctatgag                                                 20

<210> SEQ ID NO 2
<211> LENGTH: 20
<212> TYPE: DNA
<213> ORGANISM: Artificial
<220> FEATURE:
<223> OTHER INFORMATION: PCR primer

<400> SEQUENCE: 2
cctctatcgc cacattgctc                                                 20

<210> SEQ ID NO 3
<211> LENGTH: 20
```

```
-continued

<212> TYPE: DNA
<213> ORGANISM: Artificial
<220> FEATURE:
<223> OTHER INFORMATION: PCR primer

<400> SEQUENCE: 3
agatgaccta ggatgggagg                                              20

<210> SEQ ID NO 4
<211> LENGTH: 20
<212> TYPE: DNA
<213> ORGANISM: Artificial
<220> FEATURE:
<223> OTHER INFORMATION: PCR primer

<400> SEQUENCE: 4
gtgtgcactg tgattcagac                                              20
```

PRESERVATION OF RNA IN A BIOLOGICAL SAMPLE

This application claims the benefit of Provisional Application No. 60/465,307, filed Apr. 25, 2003.

FIELD OF THE INVENTION

The present invention relates to methods for preserving RNA in a biological sample undergoing analysis. More particularly, the present invention relates to methods of analyzing nucleic acid expression patterns involving the preservation of RNA in biological samples in histochemical assays.

BACKGROUND OF THE INVENTION

In the study of diseases, cell or tissue heterogeneity has limited the information available from analysis of biological samples. It has become increasingly important to be able to investigate mRNA expression patterns within specific cell populations at a specific physiological state.

Histochemical approaches have been applied to identify specific cell populations within a biological sample. See, e.g., Okuducu et al. (2003), *International Journal of Molecular Medicine* 11:449–453. Such approaches include, e.g., techniques of immunohistochemistry that detect proteins, in-situ hybridization that measures messenger RNA, and fluorescence in-situ hybridization (FISH) that detects changes in DNA. For example, histochemical methods may be used to identify a cell type, e.g., microglia in the brain as identified by the expression of complement receptor 3 (Graeber et al. (1988), *J Neurosci Res* 21:18–24), or to identify a specific cell state, e.g., cellular activation stage as shown by c-Fos expression (Sagar et al. (1988), *Science* 240:1328–1331).

Following the identification of specific cell populations at a specific physiological state by histochemical analysis, mRNA expression patterns of cells of interest can be analyzed by traditional in-situ hybridization, which is often limited to detecting the expression of only one or very few genes. Alternatively, bioarray gene profiling can be performed. Cells of interest can first be isolated via techniques such as laser capture microdissection (LCM). mRNA can be extracted, amplified, and reverse transcribed from the isolated cells. The resulting cDNAs can be hybridized to a gene microarray chip. The resultant pattern of hybridized nucleic acid provides information regarding the genetic profile of the sample tested. This approach can be used to examine the expression of multiple genes within individual cells or tissues, and can be combined with other studies such as electrophysiological, pharmacological and anatomical (retrograde labeling) studies.

Analyses of gene expression patterns of an identified cell or tissue type make it possible to directly correlate gene expression with functional changes and lesion morphology at the target cells or tissue. Results from such analyses can provide important information on the effects of a drug within a biological test system and help to elucidate mechanisms of drug-induced toxicity and organ dysfunction, which are of great importance to the field of drug discovery.

Unfortunately, RNA content has been shown to be severely depleted during histochemical assays, for example, by immunostaining of tissue sections (Fink et al. (2000), *Lab Invest* 80:327–333; Kohda et al. (2000), *Kidney Int* 57:321–331). This has practically precluded mRNA expression analysis of immunostained tissue, either by in situ hybridization or by microarray gene profiling.

It was generally assumed that RNA in tissue sections was degraded by endogenous RNases during the immunostaining protocol (Murakami et al. (2000), *Kidney Int* 58:1346–1353). Therefore, to preserve RNA in the tissue section during an immunostaining, large amounts of RNase inhibitors (Murakami et al. (2000), supra) or various tissue fixatives such as formalin (Fink et al. (2000), supra) have been used in modified immunostaining protocols. See, e.g., U.S. Patent Application Publication No. US 2002/0009768. Although these protocols have had varying degrees of success, in general they have to be extremely short in duration (Fend et al. (1999), *Am J Pathol* 154:61–66). These modified immunostaining protocols have limited usefulness because a longer incubation period is required for the better sensitivity of immunostaining detection.

Accordingly, a method to robustly preserve RNA in a biological sample is needed to facilitate investigation of mRNA expression patterns within a specific cell population or tissue.

SUMMARY OF THE INVENTION

In one general aspect, the invention relates to a method of analyzing a biological sample comprising: preserving RNA in the biological sample by incubating the biological sample with an RNA preservative in an aqueous solution so as to precipitate RNA; histochemically staining the RNA-preserved biological sample; histochemically analyzing the biological sample to identify specific cell populations; and analyzing mRNA expression patterns of the identified cells by a method comprising in-situ hybridization, or isolating identified cells and subjecting the isolated cells to bioarray gene profiling. In a preferred embodiment, the histochemically analyzing comprises subjecting the biological sample to a histochemical assay selected from: in situ hybridization for detecting mRNA; fluorescence in-situ hybridization for detecting DNA; immunocytochemistry assay for detecting proteins; enzyme histochemistry assay for measuring catalytic activities of enzymes; ligand-binding autoradiography for studying receptor-ligand interactions; and glycohistochemistry assay for detecting carbohydrate-modified substances.

In another general aspect, the invention pertains to a method of analyzing a biological sample comprising: (a) contacting the biological sample with an RNA-preserving solution comprising an aqueous solvent and an RNA preservative; (b) incubating the biological sample with a buffer solution comprising an aqueous buffered solvent and a binding agent capable of binding to the biological sample; (c) detecting the binding agent bound to the biological sample; and (d) identifying a target cell or tissue within the biological sample based on the binding pattern of the binding agent bound to the biological sample. The method may further comprise: (e) contacting the biological sample with a labeled nucleic acid molecule capable of hybridizing to mRNA of the target cell or tissue under stringent hybridization conditions; and (f) detecting the labeled nucleic acid molecule bound to the target cell or tissue. In an alternative preferred embodiment, the method further comprises: (e) isolating the target cell or tissue from the biological sample (e.g., using laser capture microdissection); (f) extracting mRNA from the isolated target cell or tissue; and (g) analyzing the extracted mRNA by gene expression bioarray analysis.

In a preferred embodiments, the RNA preservative is selected from triphenylmethane dyes (e.g., methyl green, crystal violet, and pararosaniline), cresyl violet, polyamines, and cobalt ions.

Other aspects, features and advantages of the invention will be apparent from the following disclosure, including the detailed description of the invention and its preferred embodiments and the appended claims.

BRIEF DESCRIPTION OF THE DRAWINGS

FIG. 2. This urea-agarose gel picture demonstrates the precipitation of RNA from aqueous solution by tris(4-aminophenyl)methane. RNA in each sample was analyzed by urea-agarose gel analyses after dissolving the sample in urea gel load buffer. The samples are, lane 1: RNA Size Standard; lane 2: positive control, RNA from bacteriophage MS2; lane 3: RNA precipitate which was formed when MS2 RNA was mixed with tris(4-aminophenyl)methane, and was collected as the pellet after centrifuging the mixture; lane 4: negative control 1, the presumed "pellet" which was collected by centrifuging MS2 RNA only; lane 5: negative control 2, the presumed "pellet" which was collected by centrifuging tris(4-aminophenyl)methane only.

FIG. 5. This is a dendrogram of clustered microarray data. The dendrogram indicates how closely related the conditions were based on their gene expression profile. The most related conditions were the two samples in the middle, one immunostained and one non-stained, indicating that immunostaining with RNA fixation did not alter the representation of mRNAs in the tissue sample.

DETAILED DESCRIPTION OF INVENTION AND ITS PREFERRED EMBODIMENTS

All publications cited below are hereby incorporated by reference. Unless defined otherwise, all technical and scientific terms used herein have the same meaning as commonly understood to one of ordinary skill in the art to which this invention pertains.

As used herein, the terms "comprising", "containing", and "including" are used in their open, non-limiting sense.

A "biological sample" as used herein refers to a sample containing or consisting of cell or tissue matter, such as cells or biological fluids isolated from a subject. The subject can be a eukaryotic organism, such as an animal, a plant, a worm, or a yeast cell. Alternatively, the subject can be a prokaryotic organism, such as a bacterial cell or an archaeal cell. Preferably, the subject is a mammal, such as a rat, a mouse, a monkey, or a human, who has been the object of treatment, observation or experiment. Examples of biological samples include, for example, sputum, blood, blood cells (e.g., white blood cells), amniotic fluid, plasma, semen, bone marrow, tissue or fine-needle biopsy samples, urine, peritoneal fluid, pleural fluid, and cell cultures. Biological samples may also include sections of tissues such as frozen sections taken for histological purposes.

In preferred embodiments, the biological sample is a "clinical sample," which is a sample derived from a human patient. A biological sample may also be referred to as a "patient sample." A test biological sample is the biological sample that has been the object of analysis, monitoring, or observation. A control biological sample can be either a positive or a negative control for the test biological sample. Often, the control biological sample contains the same types of tissues, cells and biological fluids as that of the test biological sample.

An "RNA preservative" as used herein refers to an agent that is capable of precipitating RNA in an aqueous solution. Methods for identifying RNA preservatives as well as examples of RNA preservatives are described below.

A "histochemical assay" as used herein refers to a biological assay useful for studying the biochemical composition of tissues or cells by means of detecting a specific labeling that correlates to a particular biochemical composition of the tissues or cells. Such an assay is useful in identifying a particular cell or tissue type based on studies of the biochemical composition of tissues or cells. There are a variety of types of histochemical assays, including, for example, in situ hybridization for the detection of mRNA, fluorescence in-situ hybridization (FISH) for the detection of DNA, immunocytochemistry for the detection of proteins, enzyme histochemistry (EH) for measuring the catalytic activity of enzymes, ligand-binding autoradiography (LB) for the study of receptor-ligand interactions, and glycohistochemistry for the detection of carbohydrate-modified substances, e.g., glycoprotein.

An "in situ hybridization assay" is a biological assay that histochemically detects a DNA or RNA sequence within cells or tissues using labeled nucleic acid probes with base sequence complementary to that of the target DNA or mRNA. Over the decades, in situ hybridization has been used extensively to study the distribution of mRNA species of particular genes within specific compartments of a cell or tissue. Types of nucleic acid probes used for in situ hybridization assay include single-stranded oligonucleotides (usually 30–40 bases in length), either singly or as cocktails, single-stranded RNA probes (riboprobes) about 300 bases long, or double-stranded cDNA sequences of various lengths. Probes can be designed specifically against any known expressed nucleic acid sequence. A number of different radioisotope and non-isotopic labels are commercially available that may be used in in-situ hybridization. For a review of known in-situ hybridization methods, see McNicol et al. (1997), *J. Pathol* 182(3):250–61.

One exemplary in situ hybridization (ISH) assay involves: fixing tissue with a formaldehyde solution, acetylating the tissue with acetic anhydride in triethanolamine-HCl solution, dehydrating the tissue with ethanol, and delipidating the tissue with chloroform; incubating the tissue with radioactively or fluorescently labeled nucleic acid probes in an aqueous buffer to allow hybridization between the probes and their complementary mRNA or DNA under stringent hybridization conditions; washing off the unbound probes by an aqueous buffer; and detecting the probes that bind to the tissue by autoradiography. "Stringent hybridization conditions" has the meaning known in the art, as described in Sambrook et al., *Molecular Cloning: A Laboratory Manual*, Second Edition, Cold Spring Harbor Laboratory, Cold Spring Harbor, N.Y., (1989). Exemplary high stringency or stringent hybridization conditions include, e.g.: 50% formamide, 5×SSC and 1% SDS incubated at 42° C., or 5×SSC and 1% SDS incubated at 65° C., with a wash in 0.2×SSC and 0.1% SDS at 65° C.

"Fluorescence in situ hybridization" or "FISH" as used herein refers to a type of in situ hybridization which involves hybridization of chromosome-specific, fluorescently labeled DNA probes to target sequences, so that the target sequences are stained or painted with fluorescent dyes and their chromosomal locations and sizes can be determined using fluorescence microscopy. The DNA probes can be for the whole chromosome or centromere, or locus-specific. The use of variable FISH techniques enhances the thorough interpretation of numerical and complex chromosome aberrations, bridging the gap between conventional chromosome banding analysis and molecular genetic DNA studies. This staining is sufficiently distinct that the hybridization signal can be seen both in metaphase spreads and in interphase nuclei (see, e.g., review by Jiang et al. (2000), *Diagn Mol Pathol* 11(1):47–57).

An "immunohistochemistry assay" or "immunostaining assay" is a biological assay that histochemically localizes immunoreactive substances within cells or tissues using antibodies. The immunoreactive substances can be any biological material that can serve as an antigen and elicit an immune response. Exemplary immunoreactive substances are proteins or small peptide haptens. Primary antibodies may be monoclonal or polyclonal in origin. Various primary antibodies are available commercially and through specialist laboratories. Also, antibodies may be directed against synthetic peptide sequences within a relatively short time scale, enabling a greater degree of flexibility for studying new targets of interest. A number of complete assay kits are also available in which all reagents necessary for the immunohistochemical detection of specific protein targets are included, usually with an optimized protocol.

For a review of immunohistochemical methods, see Swanson (1988), *Am J Clin Pathol* 90(3):333–9. An exemplary immunohistochemistry assay involves: fixing a biological sample in a fixative (e.g., acetone, alcohol, formalin, or paraformaldehyde); incubating the sample with a primary antibody in an aqueous solution to allow specific binding of the antibody to an antigen within the sample; washing off the unbound antibody; contacting the sample with a labeled secondary antibody or other agent (such as bacterial protein A) to allow specific binding of the secondary antibody or other agent to the primary antibody; washing off the unbound secondary antibody or other agent; and detecting the amount of labeled secondary antibody or other agent remaining with the sample. The detection step may be done by chromogenic detection—e.g. the secondary antibody is labelled with an enzyme such as horseradish peroxidase or alkaline phosphatase, which is detected using an enzyme substrate such as 3,3'-diaminobenzidineor nitroblue tetrazolium chloride/5-bromo-4-chloro-3-indolyl-phosphate (toluidine salt), respectively. This gives a colored precipitate that is visible under light microscopy.

An "enzyme histochemistry assay" is a biological assay that histochemically measures the catalytic activity of enzymes within cells or tissues using a detectable substrate for the enzyme. For a review of enzyme histochemistry assays, see Boonacker et al. (2001), *J. Histochem Cytochem*, 49(12):1473–86. Exemplary enzymes are proteases. In some embodiments, the substrate is radioactively labeled, chromogenic, or fluorogenic.

A "ligand-binding autoradiography" is a biological assay that histochemically measures receptor-ligand interactions using a labeled ligand. The interaction sites are localized through detection of the labeled ligand. For a review, see Sovago (2001), *Brain Res Brain Res Rev* 38(1–2):149–64.

A "glycohistochemistry assay" or "carbohydrate histochemistry assay" is a biological assay that histochemically localizes carbohydrate-modified substances, within cells or tissues. For a review, see Danguy (1995), *Eur J Histochem* 39(1):5–14. An exemplary carbohydrate-modified substance is a glycoprotein. The oligosaccharide modified glycoproteins have been studied by classical histochemical techniques such as PAS, alcian blue, and HID. More recently, lectins, a class of proteins that have specific binding sites for specific mono- or oligo-saccharides, have been applied in carbohydrate histochemistry to study tissue or intracellular localizations of carbohydrate residues. Lectins were originally obtained from the seeds of leguminous plants, and were since found in many other plant and animal sources. Different lectins that bind specifically to different monosaccharides or glycans have been identified (fucose, galactose, mannose, N-acetylglucosamine, N-acetylgalactosamine, N-acetylneuraminic acid and heparin). Lectins such as concanavalin A and wheat germ agglutinin are used as analytical and preparative agents in the study of glycoproteins.

An exemplary glycohistochemistry assay involves: fixing a biological sample in a fixative (e.g., formaldehyde); incubating the sample with a labeled lectin in an aqueous solution to allow binding of the lectin to carbohydrate residues within the sample; washing off the unbound lectin; and detecting the amount of labeled lectin remaining with the sample, such by chromogenic detection (see above).

The term "labeled", with regard to a labeled agent used in a histochemical assay such as a nucleic acid probe, antibody, lectin, or enzyme substrate, is intended to encompass direct labeling of the agent by coupling (i.e., physically linking) a detectable substance to the agent as well as indirect labeling of the agent with another reagent that is directly labeled.

Labels that are directly detectable include fluorescent labels and radioactive isotopes. Illustrative radioactive isotope labels include, e.g., $^{35}S$, $^{32}P$, and $^{3}H$. Preferred fluorescers are those absorbing light in wavelengths of from about 300 to 900 nm, more preferably from about 400 to 800 nm, and where the absorbance maximum is preferably at a wavelength ranging from about 500 to 800 nm. Exemplary fluorescers that may be used in singly labeled primers include fluorescein, rhodamine, BODIPY, cyanine dyes and the like. Fluorescers are further described in Smith et al., *Nature* (1986), 321: 647–679. Examples of indirect labeling include detection of a primary antibody using a fluorescently labeled secondary antibody, and end-labeling of a DNA probe with biotin such that it can be detected with fluorescently labeled streptavidin and the like.

"End-labeled" with regard to a labeled nucleic acid molecule means that the label moiety is present at a region at least proximal to the terminus. Preferred end labels have the moiety at the 5' terminus of the nucleic acid molecule. The labeling can also be at the 3' terminus, using for example the enzyme terminal deoxynucleotidyl transferase.

"Laser capture microdissection (LCM)" refers to a technique wherein a specimen is visualized under a microscope and then overlaid with a layer of transfer material, such as a transparent film, which when activated by a laser adheres to and extracts out specific targeted elements within the specimen for further processing. See, e.g., Emmert-Buck et al. (1996), *Science,* 274:998–1001. LCM as used herein also refers to a technique wherein, under a microscope, regions of interest in a section are outlined using a laser beam that cuts through the tissue. The region of interest is then collected, either by 'laser pressure catapulting' (see, e.g., Schutze and Lahr (1998), *Nat Biotechnol* 16:737–742.), by the force of gravity, or by being attached to a membrane that is separated from the section. Preferably, the extracted specific target elements are individual cells or tissues within complex tissues. The extracted cells or tissues may be placed directly into DNA, RNA, or protein-extraction buffer for processing.

LCM has been used to extract mRNA from frozen tissues after a rapid immunostaining method of frozen sections (see Krizman et al. (1996), *Cancer Res,* 56: 5380–5383). The method allows for an ultra-specific LCM of frozen tissues. This technique may be useful to analyze specific cell subtypes, such as basal cells in prostate or various subcomponents of an inflammatory infiltrate (e.g., T- or B-cells). This technique may also be useful in the identification and isolation of cells from a similar population differing by their metabolic state. For example, PCA cells that are proliferative may be determined by Ki-67 (MIB-1) immunostaining. This technique may also be useful in identifying cells that are morphologically difficult to identify using standard LCM protocols. However, the rapid immunostaining method may limit the sensitivity and usefulness of this technique, as many immunostaining protocols require longer incubation periods.

Methods on LCM analysis are known to those skilled in the art. References on such methods can be found from literature (for example, see Emmert-Buck et al. (1996), supra; Krizman et al. (1996), supra); and U.S. Pat. No. 6,420,132, which discloses a method and apparatus for microdissection of targets within tissue or other specimen samples smaller than approximately 10 microns in diameter).

"Bioarrays" as used herein refers to a substrate, e.g., a substantially planar substrate such as a biochip or gene chip, having a plurality of polymeric molecules spatially distributed over, and stably associated with or immobilized on, the surface of the substrate. Bioarrays of both polypeptides and polynucleotides have been developed and found use in a variety of bioarray applications, such as screening and DNA sequencing and gene expression analysis.

"Gene expression bioarray analysis" refers to an assay wherein a bioarray of "probe" oligonucleotides is contacted with a nucleic acid sample of interest, e.g., a target sample, such as poly A mRNA from a particular tissue type, or a reverse transcript thereof. See, e.g., Nees et al. (2001), *Curr Cancer Drug Targets,* 1(2):155–75. Contact is carried out under hybridization conditions and unbound nucleic acid is removed. The resultant pattern of hybridized nucleic acid provides information regarding the genetic profile of the sample tested. Gene expression analysis can measure expression of thousands of genes simultaneously, providing extensive information on gene interaction and function. Gene expression analysis may find use in various applications, e.g., identifying expression of genes, correlating gene expression to a particular phenotype, screening for disease predisposition, and identifying the effect of a particular agent on cellular gene expression, such as in toxicity testing.

Exemplary bioarray formats include oligonucleotide arrays, spotted arrays, microarrays (an array that is miniaturized so as to require microscopic examination for visual evaluation), and macroarrays (an array that is large enough to permit visual evaluation without the aid of a microscope). Methods on gene expression bioarray analysis are known to those skilled in the art. See, e.g., review by Yang et al. (2002), *Nat Rev Genet* 3(8): 579–88), and U.S. Pat. No. 6,004,755, which discloses methods on quantitative gene expression analysis using a DNA microarray.

In performing histochemical assays a conventional fixative may function by chemically introducing cross-links between molecules in the sample, for example by using glutaraldehyde. The fixative may also function by precipitating molecules in the sample, for example, by using ethanol or acetone. For a discussion of fixatives, see U.S. Patent Application Publication No. US 2002/0009768 A1. However, chemical cross-linking is undesirable for preserving RNA in the tissue, as it may impede the final extraction of RNA or even break the RNA strand (Goldsworthy et al. (1999), *Mol Carcinog* 25:86–91; Kohda et al. (2000), *Kidney Int* 57:321–331). Alcohol precipitation does not prevent the RNA precipitates from dissolving in subsequent steps involving aqueous buffers.

The present invention provides a method for preserving RNA in a biological sample during a histochemical assay wherein the biological sample is preserved with an RNA preservative that precipitates RNA in an aqueous solution. The RNA preservatives that can be used in the method of the invention precipitate RNA in aqueous buffer solutions.

The selection of a suitable RNA preservative is within the purview of those of ordinary skill in the art. For example, an RNA preservative can be identified using a method comprising: 1) contacting RNA molecules in an aqueous solution, such as water, containing buffer in which the testing compound or control is dissolved; and 2) comparing the amount of RNA precipitates in the solution containing the testing compound with that of the control. The testing compound that is capable of precipitating RNA in an aqueous solution would result in significantly more RNA precipitation than that of the control. The amount of RNA precipitation in the identification assay can be measured by methods known to those skilled in the art. An example of using such method is illustrated in Example 2 below, wherein RNA molecules in water were first contacted with a testing compound, RNA precipitates were then isolated by centrifugation, and the amount of isolated RNA precipitates was quantified by gel electrophoresis. Alternatively, the amount of RNA precipitates can be measured by light scattering in the aqueous solution following a procedure similar to that described previously for studying DNA condensation by polyamines (Vijayanathan et al. (2001), *Biochemistry* 40:13644–13651).

It has been described that triphenylmethane compounds, such as methyl green, bind double-stranded nucleic acids (Adams (1968), *J Pharm Pharmacol* 20:Suppl:18S+; Armstrong and Panzer (1972), *J Am Chem Soc* 94:7650–7653; Muller and Gautier (1975), *Eur J Biochem* 54:385–394;

Melnick and Pickering (1988), *Biochem Int* 16:69–75; Fox et al. (1992), *Eur J Histochem* 36:263–270; and Kim and Norden (1993), *FEBS Lett* 315:61–64). Using assays described supra, it was found that triphenylmethane dyes such as methyl green, crystal violet and pararosaniline precipitate RNA. It was also found that cresyl violet, which belongs to a different chemical class, precipitates RNA as well. In addition, cobalt ions were also found capable of precipitating RNA. Thus, compounds from different chemical classes and even ions are capable of precipitating RNA from aqueous solutions.

Preferably, the RNA preservatives used in the method of the invention precipitate RNA in aqueous buffer solutions, but do not interfere with the subsequent RNA extraction or RNA analysis. More preferably, the RNA preservatives precipitate RNA in aqueous buffer solutions, but do not interfere with the subsequent RNA extraction or RNA analysis, and are compatible with immunohistochemistry or other types of histochemical assays. For example, preferred RNA preservatives do not interfere with antigen-antibody interaction, and do not impart a color to the biological sample that would mask the chromogen used for immunostaining. Examples of RNA preservatives that can be used in the method of the invention include triphenylmethane dyes (such as methyl green, crystal violet, pararosaniline, or tris-(4-aminophenyl)methane), cresyl violet, polyamines, and cobalt ions.

Exemplary polyamine RNA preservatives include spermine, spermidine, 1,10-diamino-4,7-diazadecane, 1,11-diamino-4,8-diazaundecane, 1,13-diamino-4,10-diazatridecane, 1,14-diamino-4,11-diazatetradecane, 1,15-diamino-4,12-diazapentadecane, 1,16-diamino-4,13-diazahexadecane, 1,17-diamino-4,14-diazaheptadecane, 1,18-diamino-4,15-diazanonadecane, 1,19-diamino-4,16-diazaeicosane, and 1,20-diamino-4,17-diazaheneicosane.

Because RNA is preserved in the biological sample during the assay, mRNA expression patterns of a particular cell or tissue may now be analyzed after their identification by the histochemical assay. Thus, in one aspect, the present invention relates to a method of analyzing expression of an mRNA molecule at a target cell or tissue, comprising: contacting a biological sample with an RNA-preserving solution comprising an aqueous solvent and an RNA preservative; incubating the biological sample with an incubation buffer comprising a buffered aqueous solution and an agent capable of binding to the biological sample; detecting the binding agent bound to the biological sample; identifying target cell or tissue within the biological sample based on the binding pattern of the binding agent bound to the biological sample; contacting the biological sample with a labeled nucleic acid molecule capable of hybridizing to the mRNA of the target cell or tissue under stringent hybridization conditions; and detecting the labeled nucleic acid molecule bound to the target cell or tissue.

Preferably, the contacting of the biological sample with an RNA-preserving solution is performed before exposing the biological sample to the aqueous incubation buffer. The method may further comprise fixing the biological sample in a fixative, such as acetone, alcohol, formalin, or glutaraldehyde, with the RNA preservation being performed after the fixing.

The type of histochemical assay can involve, for example, in situ hybridization, FISH, immunohistochemistry, enzyme histochemistry, ligand-binding autoradiography, or glycohistochemistry. Accordingly, binding agents that may be used include, for example, a labeled complementary nucleic acid probe, an antibody, a labeled enzyme substrate, a labeled ligand, or a labeled lectin. The contacting of the biological sample with an agent and the detecting of the agent that binds to the biological sample may be conducted using techniques known in the art. An exemplary immunohistochemistry assay is described in Example 3 below.

The invention also provides a method of analyzing expression of multiple mRNA molecules at a target cell or tissue within a biological sample, comprising: contacting a biological sample with an RNA-preserving solution comprising an aqueous solvent and an RNA preservative; incubating the biological sample with an incubation buffer comprising a buffered aqueous solution and an agent capable of binding to the tissue or cell matter in the biological sample; detecting the binding agent bound to the biological sample; identifying the target cell or tissue within the biological sample based on the binding pattern of the agent bound to the biological sample; isolating the target cell or tissue from the biological sample; extracting RNA from the isolated target cell or tissue; and analyzing the extracted mRNA by gene expression bioarray analysis.

Any one or a combination of the histochemical analyses techniques described herein can be used to identify the target cell or tissue. For example, identification of the target cell or tissue can be based on a specific gene expression pattern revealed by an in situ hybridization assay, a specific protein expression pattern revealed by an immunohistochemistry assay, and/or a specific glycoprotein expression pattern revealed by a glycohistochemistry assay.

In preferred embodiments, two types of assays are performed to analyze mRNA expression patterns at the identified target cell or tissue after histochemical analysis. In one embodiment, in situ hybridization quantifies the mRNA expression level of a particular gene within the target cell or tissue. The measured mRNA expression level is compared with that of the protein expression level from the previous immunochemistry assay, the mRNA expression level of a different gene from the previous in situ hybridization assay, or the enzymatic activity from the previous enzyme histochemistry assay.

Previously, histochemical analysis combining immunostaining with in situ hybridization had been carried out to study the correlation of protein expression and mRNA expression (see, for example, Quan et al. (1997), *Proc. Natl. Acad. Sci. USA*, 94: 10985–10990). However, because these previous assays adopted the rapid immunostaining protocol in avoiding loss of RNA during the incubation, they had limited detection sensitivity and usefulness. In the method of the present invention, pre-treatment of the biological sample with an RNA preservative precipitates RNA within the sample. RNA molecules are not lost during the incubation and washing steps of immunostaining. Thus, higher protein detection sensitivity may now be obtained by incubating the biological sample in aqueous solution as long as needed during immunostaining while still maintaining high sensitivity for RNA detection after the immunostaining.

In another embodiment, mRNA expression patterns of multiple genes within the identified target cell or tissue are analyzed by first isolating the identified cell or tissue from the biological sample and then analyzing the extracted RNA by gene expression bioarray analysis. Such a method allows gene profiling on a particular cell, cell type, and tissue.

Target cell or tissue matter can be isolated from the biological sample by several approaches. In the past, this has been done through microdissection with 30-gauge needles (Vocke, et al. (1996), *Cancer Res* 56: 2411–2416). Recent advances in microdissection techniques include manual techniques, laser microdissection, laser capture microdissection (LCM), and laser catapulting (Eltoum et al. (2002), *Adv Anat Pathol*, 9(5):316–22).

LCM is effective in the molecular analysis of complex tissues because it combines the topographic precision of microscopy with the power of molecular genetics, genomics, and proteomics. As described above, LCM is a technique that is capable of isolating individual cells or tissues from complex tissues using laser capture microdissection. Laser capture microdissection occurs where the transfer polymer film is placed on a substrate overlying visualized and selected cellular material from a sample for extraction. The transfer polymer film is focally activated (melted) with a pulse brief enough to allow the melted volume to be confined to that polymer directly irradiated. Methods of LCM, such as contact LCM or non-contact LCM, using either condenser-side (or beam passage through polymer before tissue) or epi-irradiation (or laser passage through tissue before polymer), and other LCM techniques can be used in the present invention. Example 4 illustrates the use of an exemplary LCM technique.

In obtaining the sample of RNA to be analyzed from the isolated cell or tissue, the isolated cell or tissue may be subjected to a number of different processing steps. For example, such processing steps might include tissue homogenization, cell isolation and cytoplasmic extraction, nucleic acid extraction and the like, or other suitable processing steps known in the art. Techniques for isolating RNA from cells, tissues, organs or whole organisms are known in the art; see, e.g., Maniatis et al., Molecular Cloning: A Laboratory Manual (Cold Spring Harbor Press), 1989. Kits that are commercially available can also be used to extract RNA from a biological sample following the instructions provided by the manufacturer of the kit.

Standard hybridization and detection protocols are insufficient for micro- to milli-gram quantities of tissue or cells, such as those obtained from LCM. Amplification systems utilizing T7 RNA polymerase can provide multiple cRNA copies from mRNA transcripts, permitting microarray studies with reduced sample inputs. For example, an optimized T7-based amplification system for microarray analysis that yields between 200- and 700-fold amplification has been described by Pabon et al. ((2001) *Biotechniques* 31(4): 874–9).

The amplified cRNA or aRNA samples can then be reverse transcribed into target nucleic acid (cDNA), for example by priming with random hexamers under conditions sufficient for enzymatic extension of the hybridized primer.

The reverse transcribed cDNA can be labeled by using labeled primers. The label may be attached to one or more of the nucleotides in the primer, either directly or through a linking group, using methodology known in the art. In a preferred embodiment in which the label is biotin, the number of biotinylated dNTPs in the primer will be at least 1 and may be as high as 12, but will preferably be about 7. Preferably, the cDNA can be labeled by direct incorporation of fluorescently labeled dNTP, for example Cy3-dCTP, during reverse transcription of the amplified aRNA.

In preparing the end-labeled target nucleic acid (cDNA), the primer is contacted with the mRNA or cRNA with a reverse transcriptase and other reagents necessary for primer extension under conditions sufficient for first-strand cDNA synthesis. Exemplary primer-extension reagents include: dNTPs; buffering agents, e.g. Tris.Cl; cationic sources, both monovalent and divalent, e.g. KCl and $MgCl_2$; RNAase inhibitor and sulfhydryl reagents, e.g. dithiothreitol; and the like. A variety of enzymes, such as DNA polymerases, possessing reverse transcriptase activity can be used for the first-strand cDNA synthesis. Examples of suitable DNA polymerases include the DNA polymerases derived from organisms selected from thermophilic bacteria and *archaebacteria*, retroviruses, yeasts, *Neurosporas, Drosophilas*, primates and rodents. Preferably, the DNA polymerase is selected from Moloney murine leukemia virus (M-MLV) (described in U.S. Pat. No. 4,943,531) and M-MLV reverse transcriptase lacking RNaseH activity (described in U.S. Pat. No. 5,405,776), human T-cell leukemia virus type I (HTLV-I), bovine leukemia virus (BLV), Rous sarcoma virus (RSV), human immunodeficiency virus (HIV) and *Thermus aquaticus* (*Taq*) or *Thermus thermophilus* (*Tth*) (described in U.S. Pat. No. 5,322,770), avian myeloblastosis virus reverse transcriptase, and the like. Suitable DNA polymerases possessing reverse transcriptase activity may be isolated from an organism, obtained commercially or obtained from cells which express high levels of cloned genes encoding the polymerases by methods known to those of skill in the art. The particular manner of obtaining the polymerase preferably is chosen based on factors such as convenience, cost, availability and the like. Of particular interest because of their commercial availability and well characterized properties are avian myeloblastosis virus reverse transcriptase and M-MLV.

The order in which the reagents are combined in performing reverse transcription may be modified as desired. One protocol that may be used involves the combination of all reagents, except for the reverse transcriptase on ice, followed by addition of the reverse transcriptase and mixing at around 4° C. After mixing, the temperature of the reaction mixture is raised to 37° C. followed by incubation for a period of time sufficient for first-strand cDNA primer extension product to form, e.g., about 1 hour.

The reverse transcripts (cDNA) from the reverse transcription can be further amplified by polymerase chain reaction following standard protocols known to those skilled in the art.

The extracted mRNA can be reverse transcribed and amplified by multiplex quantitative reverse transcription-polymerase chain reaction (RT-PCR), a form of RT-PCR that involves the simultaneous amplification of more than one reverse transcript of a target mRNA per reaction by mixing multiple primer pairs with different specificities. The labeled cDNA that has been reverse transcribed from target mRNA nucleic acids is contacted with an array of polynucleotide probes stably associated with the surface of a substantially planar solid support (chip) under hybridization conditions sufficient to produce a hybridization pattern of complementary probe/target complexes. A variety of different arrays known in the art may be used in the present invention.

The polymeric or probe molecules of the arrays which are capable of sequence specific hybridization with target nucleic acid may be polynucleotides or hybridizing analogues or mimetics thereof, for example: nucleic acids in which the phosphodiester linkage has been replaced with a substitute linkage, such as phosphorothioate, methylimino, methylphosphonate, phosphoramidate, guanidine and the like; nucleic acids in which the ribose subunit has been substituted, e.g., hexose phosphodiester; peptide nucleic acids; and the like. The length of the probes stably associated with the chip will generally range from 10 to 1000 nts. In some embodiments, the probes are oligonucleotides ranging from 15 to 150 nts, preferably from 15 to 100 nts in length. In other embodiments the probes are longer, ranging in length from 150 to 1000 nts, where the polynucleotide probes may be single- or double-stranded, preferably double-stranded, and may be PCR fragments amplified from cDNA.

The probe molecules on the surface of the substrates preferably correspond to known genes of the physiological source being analyzed and are positioned on the array at a known location so that positive hybridization events may be correlated to expression of a particular gene in the physiological source from which the target nucleic acid sample is derived. Because of the manner in which the target nucleic acid sample is generated, as described below, the arrays of probes will preferably have sequences that are complementary to the non-template strands of the gene to which they correspond.

The substrates with which the probe molecules are stably associated may be fabricated from a variety of materials, such as plastics, ceramics, metals, gels, membranes, glasses, and the like. The arrays may be produced according to any convenient methodology, such as preforming the probes and then stably associating them with the surface of the support or growing the probes directly on the support. A number of different array configurations and methods for their production and usage are known in the art. See, e.g., U.S. Pat. Nos. 5,445,934; 5,532,128; 5,556,752; 5,242,974; 5,384,261; 5,405,783; 5,412,087; 5,424,186; 5,429,807; 5,436,327; 5,472,672; 5,527,681; 5,529,756; 5,545, 531; 5,554,501; 5,561,071; 5,571,639; 5,593,839; 5,599,695; 5,624,711; 5,658,734; and 5,700,637.

In embodiments of assays of the subject invention, the labeled target nucleic acid is contacted with the array under conditions sufficient for hybridization of target nucleic acid to probe to occur. Suitable hybridization conditions are well known to those of skill in the art and reviewed in Maniatis et al, supra, and WO 9521944. The conditions can be modified to achieve a desired specificity in hybridization, e.g. highly stringent or moderately stringent conditions. For example, low stringency hybridization conditions may be at 50° C. and 6×SSC (0.9 M sodium chloride/0.09 M sodium citrate), while hybridization under stringent conditions may be at 50° C. or higher and 0.1×SSC (15 mM sodium chloride/0.15 mM sodium citrate).

Following hybridization, where non-hybridized labeled nucleic acid is capable of emitting a signal during the detection step, a washing step is employed where unhybridized labeled nucleic acid is removed from the support surface, generating a pattern of hybridized nucleic acid on the substrate surface. A variety of wash solutions and protocols for their use are known to those of skill in the art and may be used. Example 5 illustrates a procedure for performing gene profiling using microarray analysis.

The resultant hybridization pattern(s) of labeled nucleic acids may be visualized or detected in a variety of ways. The particular manner of detection is preferably chosen based on the particular label of the nucleic acid, and exemplary detection techniques include scintillation counting, autoradiography, fluorescence measurement, calorimetric measurement, light emission measurement and the like.

To further illustrate the invention, the following examples are provided.

EXAMPLE 1

RNA Diffusion into the Tissue Incubation Buffer During Immunostaining

To characterize the mechanism by which RNA is lost from the tissue sections during immunostaining, RNA from immunostained tissue sections was extracted and compared to that from tissue sections that had not undergone immunostaining. Frozen sections were air-dried and fixed in cold acetone for 2 min. After a quick rinse in phosphate buffered saline (0.137 M NaCl, 0.0027 M KCl, 0.01 M phosphate buffer pH 7.4, PBS), sections were incubated in methyl green solution (Vector, Burlingame, Calif.) for 2 min. They were then rinsed in PBS and incubated in OX-42 antibody (Serotec, Raleigh, N.C.) diluted 1:100 in PBS with 0.5% acetylated BSA (Sigma) for 5 min. Sections were rinsed in PBS and then incubated in biotinylated goat anti-mouse antibody (Chemicon, Temecula, Calif.) diluted 1:100 in PBS with 0.5% acetylated BSA for 5 min. After rinsing in PBS, sections were incubated in 0.1 M Tris-HCl, pH 8.0 for 1 min and then transferred to PBS with alkaline phosphatase-streptavidin (Vector), diluted 1:100, and incubated for 5 min. Sections were then rinsed in PBS and colour was developed for 10 min using fuchsin red (Dako, Carpinteria, Calif.) as the substrate. Sections were rinsed in RNase-free water and quickly counterstained with Mayer's Hematoxylin. After subsequent washes in PBS and water, the sections were dehydrated through increasing concentrations of ethanol and finally xylene. Sections were left to air dry. Sections were scraped off from the slide into a 1.5-ml Eppendorf tube and RNA was extracted using the Rneasy kit (Qiagen, Alameda, Calif.) according to the manufacturer's protocol. For RT-PCR, 10 µl of the extracted RNA (from a total volume of 30 µl) was mixed with 1 µg oligo-dT primer (Operon, Alameda, Calif.) and heated to 70° C. for 10 minutes (min), and then cooled on ice. cDNA was synthesized using Superscript II (200 u/reaction) (Invitrogen, Carlsbad, Calif.) in 50 mM Tris-HCl, 75 mM KCl, 3 mM $MgCl_2$, 20 mM DTT, 500 µM dNTPs and 40 units of RNase Block (Stratagene, La Jolla, Calif.) in a 20-µl reaction for 2 hours at 42° C. The reaction was terminated by incubating at 70° C. for 10 min. Real time quantitative PCR was performed using a Smartcycler (Cepheid, Sunnyvale, Calif.). An aliquot of the cDNA was removed and diluted 4-fold. Two µl of the dilution was used for real time PCR analysis. The mix contained 2 U ExTaq (Panvera, Madison, Wis.), 0.2×SybrGreen (Molecular Probes, Eugene, Oreg.), 0.4 µM of each primer, 200 mM dNTPs (Amersham, Piscataway, N.J.), 2–4 mM $MgCl_2$ (depending on primers), 0.12 mg/ml BSA (Sigma), 90 mM trehalose (Sigma) and 0.12% Tween 20 (Sigma) in 10 mM Tris-HCl pH 8. The PCR parameters were 95° C./90 sec, 40 cycles of 95° C./5 sec, 54–70° C. (depending on primers)/7 sec and 72° C./15 sec. At the end of each program a melt curve analysis was done.

Fragmentation of RNA, whether by RNase activity, mechanical shearing or chemical hydrolysis, cleaves the polynucleotide internally at random locations (though different RNases will preferentially cleave adjacent to certain bases). Increasing fragmentation of RNA will result in progressively shorter strands of cDNA produced by priming from the 3'-end of the RNA using an oligo-dT primer. The length of cDNA product can be detected by real time quantitative PCR directed towards different amplicons from the 5'-end and the 3'-end portions of the mRNA. The shorter the average length of the population of individual cDNA molecules for a given mRNA, the more biased the cDNA will be towards the 3'-end and the lower the 5'-end/3'-end ratio will by as measured by PCR.

To detect fragmentation of RNA in the tissue section during immunohistochemistry, two pairs of primers were designed for rat neuron specific enolase (NSE, GenBank DNA Accession No: AF019973, 2222 bases in total). One primer pair directed to the 5'-end portion of the mRNA (bases 184–474 of the NSE mRNA), SEQ ID NO: 1, 5'-CCTCCACTGGCATCTATGAG-3' and SEQ ID NO: 2, 5'-CCTCTATCGCCACATTGCTC-3'; and the other directed to the 3'-end portion of the mRNA (bases 1936–2221 of the NSE mRNA), SEQ ID NO: 3,5'-AGAT- GACCTAGGATGGGAGG-3' and SEQ ID NO: 4,5'-GTGT-GCACTGTGATTCAGAC-3'.

The amount of RNA in immunostained tissue, judged by PCR against the 3'-end portion of the NSE mRNA, was merely 6% of the non-immunostained tissue. Thus 94% of NSE mRNA, and likely of total mRNA as well, was lost during the immunostaining procedure. However, the average ratios of 5'-end/3'-end PCR were nearly identical for immunostained versus non-immunostained tissue: 8.74% and 8.75% respectively. Thus, even though the majority of the RNA content was gone from the tissue section, there were no signs of RNA degradation. The conclusion was that RNA was lost during immunohistochemistry not by degradation, but by some other mechanism, likely diffusion into the solution.

Figure 1:
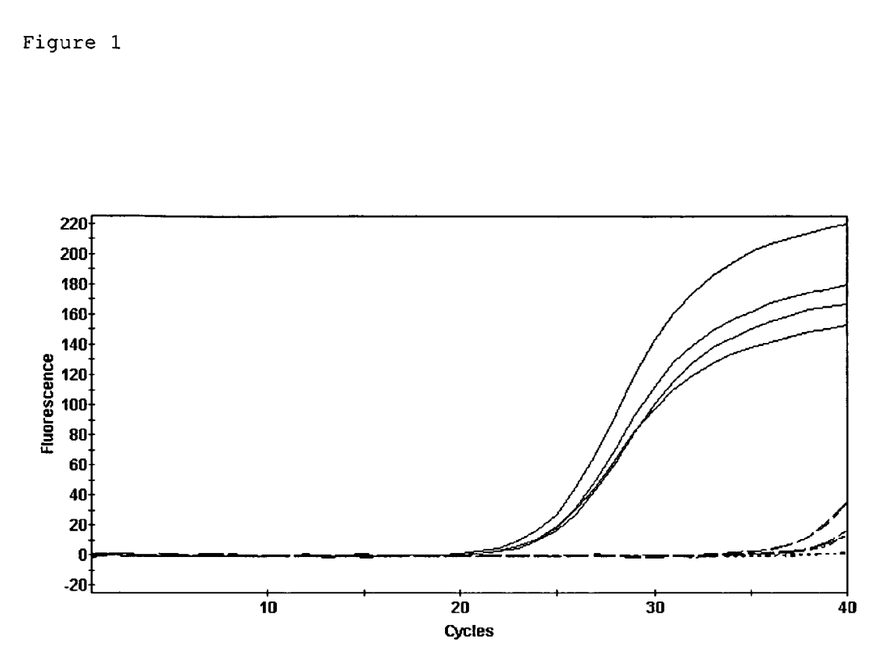
FIG. 1. This figure illustrates the accumulation of Neuron Specific Enolase (NSE) mRNA in tissue incubation buffer during immunostaining. The amount of NSE mRNA was measured as the amount of cDNA via real time PCR, as shown on the Sybr green fluorescence accumulation graphs. cDNA was synthesized from the tissue incubation buffer PBS after tissue incubation (solid black line), and before tissue incubation (dotted line). To control for potential genomic DNA in the incubation buffer, PCR was also performed without cDNA synthesis (interrupted line) from PBS after tissue incubation. Two samples for each condition and two PCR reactions for each sample were performed.
Figure 2:
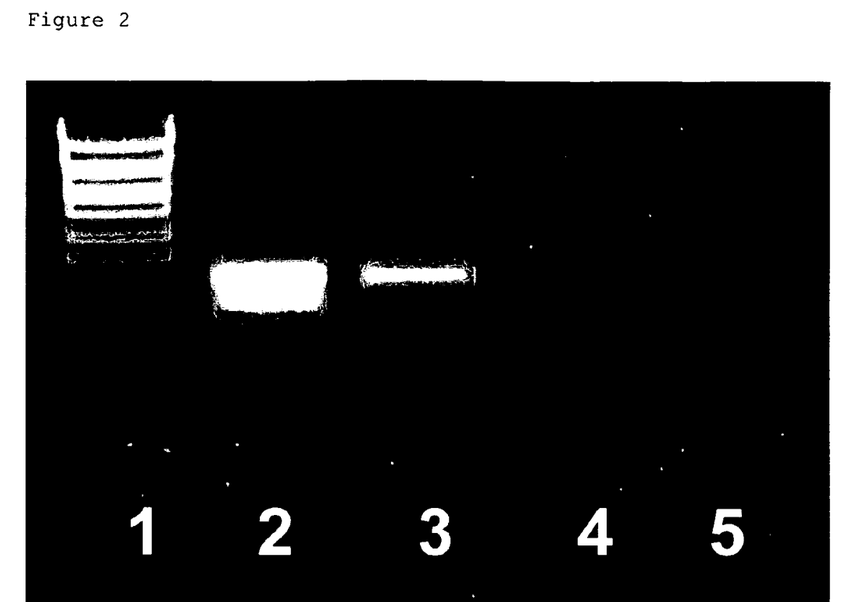

To test the hypothesis that RNA was lost by diffusion into the aqueous solution during immunostaining, the aqueous solution was collected after the immunostaining procedure. cDNA was synthesized from the phosphate buffer saline (PBS) solution that was used in the immunostaining for tissue incubation, and PCR for NSE cDNA corresponding to the 3' portion of the NSE mRNA (bases 1936–2221 of the NSE mRNA) was performed using real-time quantitative PCR. As shown in FIG. 1, NSE mRNA is clearly present in the solution after immunostaining, thereby confirming the hypothesis that RNA dissolves in aqueous buffers during incubation of the tissue section.

Thus, the primary cause for the loss of RNA during immunohistochemistry is not RNA degradation by RNases, but diffusion of the RNA into the aqueous assay buffer during incubation. The main challenge in preserving RNA during immunohistochemistry therefore is not to prevent RNase activity, but to prevent the dissolution of RNA into the aqueous buffers used.

EXAMPLE 2

Identification of RNA Preservatives

A testing compound, tris(4-aminophenyl)methane, was first incubated with RNA molecules in an aqueous solution, such as water. The mixture of the compound and RNA was then centrifuged at 10,000 g for 20 min to collect any precipitate. The collected precipitate was then analyzed by denaturing agarose gel electrophoresis. A band of the proper molecular weight (depending on the type of RNA used) indicated that the compound precipitated RNA.

Other compounds that precipitated RNA from an aqueous buffer included methyl green, cresyl violet, tris(4-aminophenyl)methane and hexamine cobalt. Compounds that were found positive by this screening assay were then tested for efficacy in preventing RNA loss during immunohistochemistry on brain tissue sections.

EXAMPLE 3

Immunohistochemical Assay (A) COMPARISON EXAMPLE

OX42 Immunostaining Without RNA Preservation

Frozen sections of tissues were air dried and fixed in cold acetone for 2 min. Sections were rinsed in PBS and incubated with OX42 antibody (Serotec, Raleigh, N.C.) diluted 1:100 in PBS with 0.5% acetylated BSA (Sigma) for 5 min. Sections were then rinsed in PBS and incubated with biotinylated goat-anti-mouse antibody (Chemicon, Temecula, Calif.), diluted 1:100 in PBS with 0.5% acetylated BSA for 5 min. Slides were again rinsed in PBS and then incubated 1 min in 100 mM Tris-HCl, pH 8. Then, slides were incubated with peroxidase-conjugated streptavidin (Jackson ImmunOResearch Laboratories, West Grove, Pa.), which was diluted 1:100 in PBS, for 5 min. Sections were rinsed in PBS, and detection was performed using AEC (DAKO, Carpinteria, Calif.) for 5 min. Sections were rinsed in water and counterstained with Mayer's Hematoxylin (BioGenex, San Ramon, Calif.) for 5 sec. Sections were rinsed in PBS, then water and finally left to air dry.

(B) INVENTIVE EXAMPLE

OX42 Immunostaining With RNA Preservation

The RNA-preserving step was inserted right after the acetone fixation in the beginning of the staining protocol of Example 3(A) above.

(i) Using methyl green as the RNA preservative, sections were at this stage rinsed in PBS (Invitrogen, Carlsbad, Calif.) and incubated in methyl green (Vector, Burlingame, Calif.) for 2 min. The staining protocol described above was then followed.

(ii) Using cresyl violet as the RNA preservative, sections were first fixed in 100% ethanol for 1 min (instead of acetone) and incubated in 95% ethanol/10 sec, 70% ethanol/10 sec, 50% ethanol/10 sec, PBS/10 sec and 0.83% cresyl violet in $H_2O$/40 sec. Sections were then immunostained as described above, starting with a PBS rinse and incubation in the primary antibody. After the final PBS rinse, the Nissl stain was destained by successive incubations in 70% ethanol/10 sec, 95% ethanol/10 sec, 95% ethanol+1.6% acetic acid/5–10 sec, 95% ethanol/10 sec and finally 100% ethanol/10 sec. If sections were used for laser capture, they were cleared by a 1 min incubation in xylene and then left to air dry.

(C) INVENTIVE EXAMPLE

IB4 Immunostaining With RNA Preservation

Frozen tissue sections were fixed in 100% ethanol for 1 min, and then rinsed in 95% ethanol, 70% ethanol and PBS. The sections were then stained in 0.83% cresyl violet in $H_2O$ for 45 sec and rinsed in PBS. Sections were then incubated with 20 µg/ml peroxidase-conjugated IB4 (Sigma) in PBS with 1% acetylated BSA for 15 min. After a PBS rinse, sections were developed with DAB (Vector) for 5 min. The reaction was stopped with a PBS rinse. The Nissl stain was destained by successive rinses in 70% ethanol, 95% ethanol, 95% ethanol+1.6% acetic acid, 100% ethanol and finally cleared in xylene for 1 min and left to air dry.

(D) Quantification of RNA After Immunohistochemistry

To measure the RNA content in tissue sections after immunohistochemistry, whole sections were scraped off into a 1.5 ml centrifuge tube. RNA was quantified by RT-PCR for the 3' portion of NSE following the procedures described in Example 1.

Figure 3:
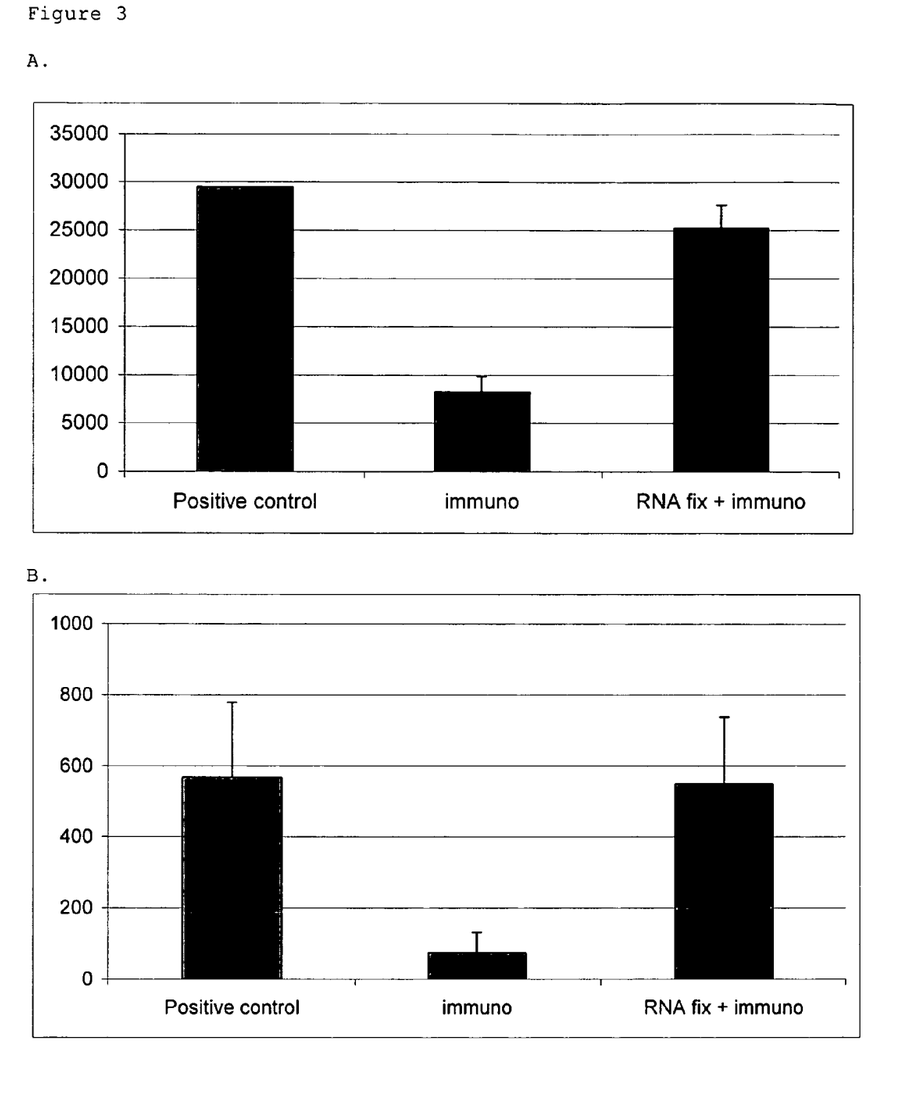
FIG. 3. This figure shows the preservation of RNA in tissue sections by RNA preservatives during immunostaining. Rat brain sections were immunostained, with-(RNA fix+immuno) or without (immuno) the step of RNA preservation. At the end of immunostaining, the tissue section was scraped off. RNA was extracted from the scraped-off tissue sections, and was quantified by RT-PCR for NSE mRNA. A) RNA preservation using methyl green. B) RNA preservation using cresyl violet.

FIG. 3A shows the RNA preservation effect of methyl green on NSE content in the tissue. After immunohistochemistry with and without methyl green pretreatment, approximately 70% of the RNA, as indicated by NSE, was lost after immunohistochemistry in the absence of methyl green, whereas the inclusion of methyl green into the assay protocol resulted in a high recovery of RNA. Thus, methyl green prevented the loss of RNA during immunohistochemistry. FIG. 3B shows a similar experiment using cresyl violet, with a similar result.

Figure 4:
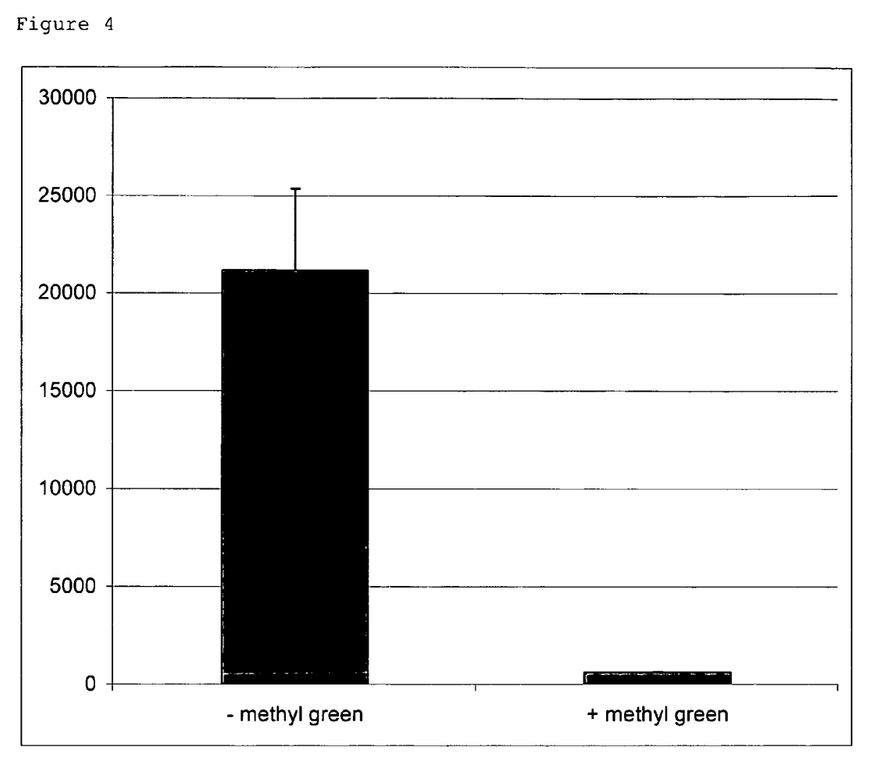
FIG. 4. This graph shows that RNA preservation decreased the amount of RNA in the incubation buffer during immunostaining. Tissue sections were treated with or without methyl green prior to immunostaining. The amount of NSE mRNA in the tissue incubation buffer after immunostaining was measured as the amount of cDNA by RT-PCR. Units on Y-axis are arbitrary. Error bars indicate standard deviation.

If these preservative compounds effectively prevent the diffusion of RNA into the staining solution, then the amount of RNA in the solution after the immunohistochemical protocol should be reduced when these compounds are used. FIG. 4 shows that this is indeed the case. Inclusion of methyl green significantly reduced the amount of NSE in the tissue incubation solution.

To be desirable RNA preservatives, the compounds used should be compatible with the particular immunohistochemistry assay being performed. That entails, e.g., neither interfering with the antigen-antibody interaction, nor imparting a color to the section that would mask the chromogen used for immunostaining. After immunostaining, sections were counterstained to visualize cell nuclei. The observations reflected that pre-treating the tissue section with methyl green did not affect the observed immunostaining results.

EXAMPLE 4

Laser Capture Microdissection (LCM)

Cells were captured using the PixCell II laser capture microdissection instrument (Arcturus, Mountain View, Calif.) onto standard caps, TF100, following manufacture's instructions. Caps were then put in 500-μl tubes and frozen on dry ice. Cells were picked from dorsal hippocampus Ca1 in coronal sections from adult female Sprague-Dawley rats. One hundred cells were picked per sample.

EXAMPLE 5

Gene Expression Profiling After Immunostaining

To test the efficacy of RNA preservation with gene expression profiling, individual cells were isolated by laser capture microdissection and were analyzed for gene expression by microarray analysis. Brain sections were pretreated with an RNA preservative, cresyl violet, immunostained with IB4, which stains microglia (Streit et al. (1990), *J Histochem Cytochem* 38:1683–1686). Cells from hippocampus Ca1 were laser-captured, with or without immunostaining. These cells were captured as they could be identified without immunostaining and thus used as a control to see the effects of immunostaining on the quality of the extracted RNA. In addition to these cells, immunopositive microglia were also laser-captured. The RNA from these laser-captured samples was amplified using a T7-based aRNA amplification method, labelled with Cy3 and hybridized onto cDNA microarrays.

Figure 5:
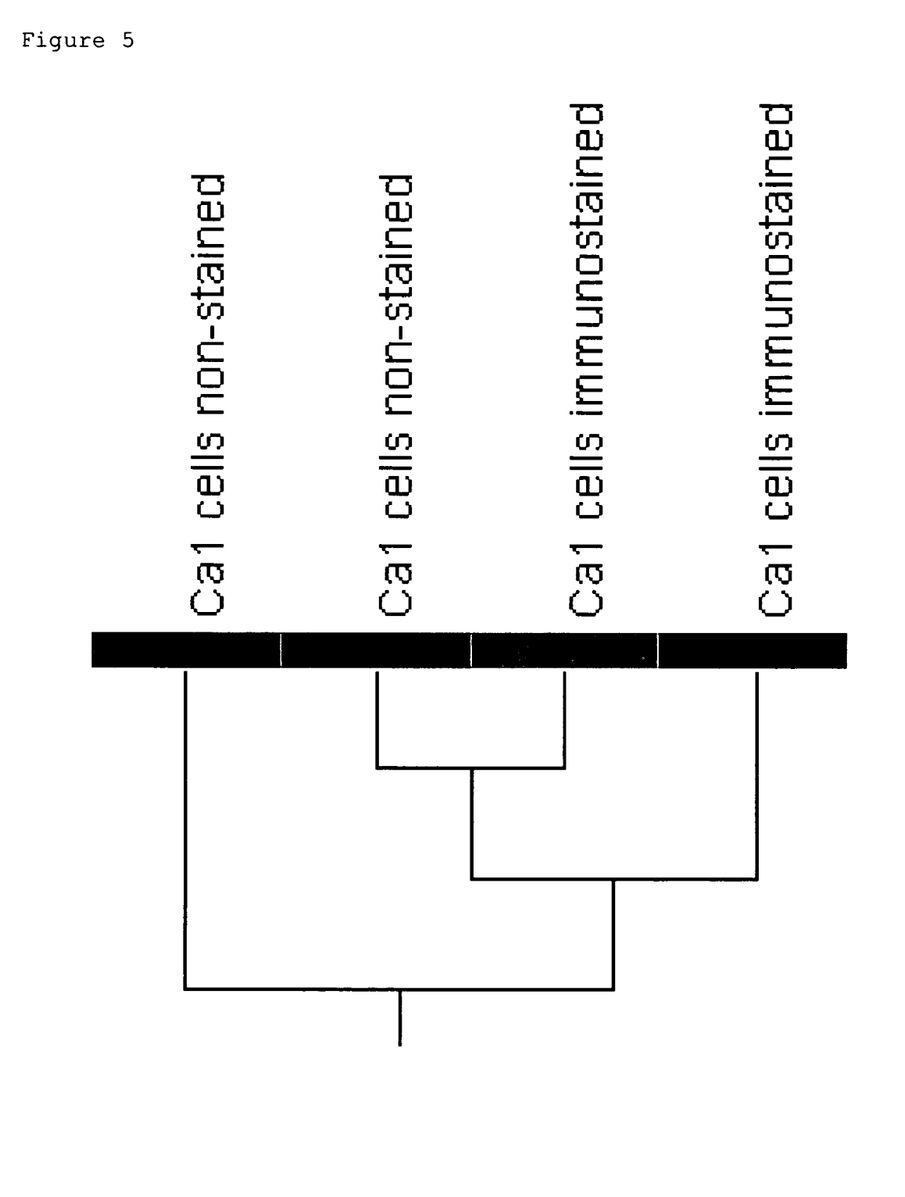

Cluster analysis of the data from hippocampus Ca1 showed that there was no portioning between the different experimental conditions, as reflected in the dendrogram in FIG. 5. As shown in the dendrogram, the one immunostained sample and one non-stained sample were most closely related. Overall, the differences between the samples were small. Cluster analysis of the microarray data did not detect any differences between immunostained and non-stained samples, showing that the RNA preservation maintained cellular RNA content without bias.

As apparent from the foregoing, the inventive methods robustly preserve RNA in a biological sample by using an RNA-preservative, providing advantageous methods for investigating mRNA expression patterns within specific cell populations or tissues.

While the above detailed description and preferred embodiments have been provided to illustrate the invention and its various features and advantages, it will be understood that invention is defined not by the foregoing, but by the following claims as properly construed under principles of patent law.

What is claimed is:

1. A method of analyzing a biological sample comprising:
   precipitating RNA in the biological sample by incubating the biological sample with an RNA preservative in an aqueous solution to yield a biological sample containing preserved RNA;
   histochemically staining the biological sample containing preserved RNA;
   histochemically analyzing the stained biological sample containing preserved RNA to identify specific cell populations; and
   analyzing mRNA expression patterns of the identified cells by a method comprising: in-situ hybridization; or isolating identified cells and subjecting the isolated cells to bioarray gene profiling.

2. A method according to claim 1, wherein the RNA preservative is selected from the group consisting of triphenylmethane dyes, cresyl violet, polyamines, and cobalt ions.

3. A method according to claim 1, wherein the RNA preservative is a triphenylmethane dye selected from the group consisting of methyl green, crystal violet, and para-rosaniline.

4. A method according to claim 1, wherein the histochemically analyzing comprises subjecting the biological sample to a histochemical assay selected from the group consisting of: in situ hybridization for detecting mRNA; fluorescence in-situ hybridization for detecting DNA; immunocytochemistry assay for detecting proteins; enzyme histochemistry assay for measuring catalytic activities of enzymes; ligand-binding autoradiography for studying receptor-ligand interactions; and glycohistochemistry assay for detecting carbohydrate-modified substances.

\* \* \* \* \*